US010593038B2

(12) United States Patent
Bauer et al.

(10) Patent No.: US 10,593,038 B2
(45) Date of Patent: Mar. 17, 2020

(54) CREATING MAGNETIC RESONANCE IMAGES

(71) Applicants: Simon Bauer, Baunach (DE); Ralf Kartäusch, Erlangen (DE); Jörg Roland, Hemhofen (DE)

(72) Inventors: Simon Bauer, Baunach (DE); Ralf Kartäusch, Erlangen (DE); Jörg Roland, Hemhofen (DE)

(73) Assignee: Siemens Healthcare GmbH, Erlangen (DE)

( * ) Notice: Subject to any disclaimer, the term of this patent is extended or adjusted under 35 U.S.C. 154(b) by 123 days.

(21) Appl. No.: 15/895,086

(22) Filed: Feb. 13, 2018

(65) Prior Publication Data
US 2018/0232880 A1    Aug. 16, 2018

(30) Foreign Application Priority Data
Feb. 16, 2017    (DE) .................. 10 2017 202 535

(51) Int. Cl.
*G06K 9/00*    (2006.01)
*G06T 7/00*    (2017.01)
(Continued)

(52) U.S. Cl.
CPC ............ *G06T 7/0012* (2013.01); *A61B 5/055* (2013.01); *G01R 33/4824* (2013.01);
(Continued)

(58) Field of Classification Search
CPC ....... G06T 7/0012; G06T 7/11; G06T 7/0014; G06T 7/248; G06T 11/005; G06T 11/006;
(Continued)

(56) References Cited
U.S. PATENT DOCUMENTS 9,675,249 B2 *  6/2017  Miyazaki ........... G01R 33/5614
10,317,499 B2 *  6/2019  Chen ................... G01R 33/5611
(Continued)

FOREIGN PATENT DOCUMENTS

DE        10337932 A1    3/2005
DE     102011086369 A1    5/2013
DE       102013205832    10/2014

OTHER PUBLICATIONS

Block, Kai Tobias et. al.: "GRASP: Tackling the Challenges of Abdominopelvic DCE-MRI"; in: MAGNETOM Flash; vol. 60, No. 5; pp. 16-22; 2014.
(Continued)

*Primary Examiner* — Jose L Couso
(74) *Attorney, Agent, or Firm* — Lempia Summerfield Katz LLC

(57) ABSTRACT

A method is provided for creating magnetic resonance images of a predetermined three-dimensional volume segment of a living object undergoing examination, using a magnetic resonance device. The method includes acquiring magnetic resonance data in the volume segment by radial acquisition of a k-space for a predetermined duration of capture that includes at least one full respiratory period of the object undergoing examination; analyzing the magnetic resonance data in order to determine therefrom at least one respiratory period; forming at least one data group that includes only the magnetic resonance data that belongs to at least one respiratory state of the at least one respiratory period; and creating the magnetic resonance images from only the magnetic resonance data of the at least one data group. Here, it is advantageous that magnetic resonance images of higher temporal resolution and/or better image quality, in particular with smaller image artifacts, may be provided.

14 Claims, 2 Drawing Sheets

(51) Int. Cl.
G01R 33/48 (2006.01)
G01R 33/563 (2006.01)
G06T 7/11 (2017.01)
A61B 5/055 (2006.01)
G01R 33/565 (2006.01)
A61B 5/08 (2006.01)
A61B 5/00 (2006.01)
G01R 33/56 (2006.01)

(52) U.S. Cl.
CPC .............. *G01R 33/563* (2013.01); *G06T 7/11* (2017.01); *A61B 5/0816* (2013.01); *A61B 5/7207* (2013.01); *G01R 33/565* (2013.01); *G01R 33/5608* (2013.01); *G01R 33/56383* (2013.01); *G06T 2207/10088* (2013.01); *G06T 2207/30061* (2013.01)

(58) Field of Classification Search
CPC ..... G06T 15/08; G06T 2210/41; A61B 5/055; A61B 5/0816; A61B 5/7207; A61B 5/113; A61B 5/7257; A61B 5/7292; A61B 5/7285; A61B 5/08; A61B 5/087; A61B 5/7289; A61B 5/004; A61B 5/082; A61B 5/091; A61B 5/1135; A61B 2560/0223; A61B 2576/02; G01R 33/4824; G01R 33/563; G01R 33/5608; G01R 33/56383; G01R 33/565; G01R 33/4826; G01R 33/5611; G01R 33/56509; G01R 33/5672; G01R 33/4822; G01R 33/56308; G01R 33/56518; G01R 33/56545; G01R 33/5673; G01R 33/5676; G01R 33/56325; G01R 33/0029; G01R 33/4818; G06K 9/00362; G06K 2209/05; G06K 2209/051; G06K 2209/40; H04N 7/18; A61N 5/1039

See application file for complete search history.

(56) References Cited

U.S. PATENT DOCUMENTS

| | | | | |
|---|---|---|---|---|
| 10,371,779 | B2* | 8/2019 | Herzka | A61B 5/4836 |
| 10,401,463 | B2* | 9/2019 | Van Den Brink | G01R 33/283 |
| 2005/0073303 | A1 | 4/2005 | Harer et al. | |
| 2012/0146641 | A1* | 6/2012 | Wu et al. | G01R 33/4826 324/309 |
| 2012/0245453 | A1* | 9/2012 | Tryggestad | A61B 6/463 600/413 |
| 2014/0039297 | A1* | 2/2014 | Keupp | G01R 33/5605 600/413 |
| 2015/0015691 | A1 | 1/2015 | Forman et al. | |
| 2015/0077112 | A1 | 3/2015 | Otazo et al. | |
| 2015/0309147 | A1* | 10/2015 | Schmitter | G01R 33/543 600/410 |
| 2016/0324500 | A1 | 11/2016 | Fan et al. | |
| 2017/0367612 | A1* | 12/2017 | Kawrykow | G06T 7/74 |
| 2019/0113587 | A1* | 4/2019 | Paulson | G01R 33/4808 |

OTHER PUBLICATIONS

Feng, Li et al: "Golden-Angle Radial Sparse Parallel MRI: Combination of Compressed Sensing, Parallel Imaging, and Golden-Angle Radial Sampling for Fast and Flexible Dynamic Volumetric MRI"; in: Magnetic Resonance Medicine; vol. 72; pp. 707-717; 2014.

Grimm, Robert et. al.: "Optimal Channel Selection for Respiratory Self-Gating Signals"; in: 3ISMRM 21st Annual Vleeting & Exhibition, SMRT 22nd Annual Meeting Apr. 20-26, 2013, Salt Lake City, Utah, USA.

Grimm, Robert et. al.: "Self-gated MRI motion modeling for respiratory motion compensation in integrated PET/MRI"; in: Medical Image Analysis; Vo. 19, pp. 110-120; 2015.

Riffel, Philipp et. al.: "Free-breathing DCE-MRI of the Kidney using GRASP"; in: MAGNETOM Flash; vol. 66, No. 3; pp. 56-58; 2016.

German Office Action cited in the corresponding German application No. DE102017202535.2; dated Oct. 24, 2018; 8 pages.

Li Feng et al, Compressed Sensing Reconstruction with an Additional Respiratory-Phase Dimension for Free-Breathing Imaging, Proc. Intl. Soc. Mag. Reson. Med. 21 (2013), P0606.

Lin, Wei et al., Respiratory Motion-Compensated Radial Dynamic Contrast-Enhanced (DCE)-MRI of Chest and Abdominal Lesions, Magnetic Resonance in Medicine; vol. 60; pp. 1135-1146; 2008.

Pang, Jianing et al, Whole-Heart Coronary MRA with 100% Respiratory Gating Efficiency: Self-Navigated Three-Dimensional Retrospective Image-Based Motion Correction (TRIM), Magnetic Resonance in Medicine 71 :67-74 (2014); D01 10.1002/mrm.24628; (c) 2013 Wiley Periodicals, Inc.

Tibiletti, Marta et al, Multistage Self-Gated Lung Imaging in Small Rodents, Magnetic Resonance in Medicine; pp. 2448-2454; DOI 10.1002/mrm.25849.

Zixin Deng et al, Four-Dimensional MRI Using Three-Dimensional Radial Sampling with Respiratory Self-Gating to Characterize Temporal Phase-Resolved Respiratory Motion in the Abdomen, Magnetic Resonance in Medicine 75:1574-1585 (2016); pp:1574-1585; (c) 2015 Wiley Periodicals, Inc; DOI 10.1002/mrm.25753.

* cited by examiner

US 10,593,038 B2

CREATING MAGNETIC RESONANCE IMAGES

The application claims the benefit of German Patent Application No. DE 10 2017 202 535.2, filed Feb. 16, 2017, which is hereby incorporated by reference in its entirety.

TECHNICAL FIELD

The present disclosure relates to a method for creating magnetic resonance images of a predetermined three-dimensional volume segment of a living object undergoing examination, using a magnetic resonance device. The disclosure also relates to a computer program product that may be loaded directly into a memory of a digital computer, including program code parts suitable for performing acts of the method. The disclosure further relates to a computer-readable storage medium, including instructions that may be executed by a computer and that are suitable for the computer to perform acts of the method. The disclosure moreover relates to a processing facility that is intended to perform the method. The disclosure may be used for capturing magnetic resonance images for tracking the course of a contrast agent, in particular, for measuring human or animal livers, kidneys, or lungs.

BACKGROUND

DE 103 37 932 A1 discloses a method for minimizing streak artifacts during modular k-space scanning in magnetic resonance imaging, wherein the method includes the following acts: defining an odd integer k-space scanning module number $N\varphi=2n+1$ that defines the number of incrementally rotated repeated modules of the k-space scanning process; selecting, by a slice selection gradient, any slice in the region of the object to be examined; and acquiring data for all $N\varphi$ angle-dependent k-space scanning modules in the selected slice such that each k-space scanning module has an azimuthal distance of $\Delta\varphi/2=360°/(2\cdot N\varphi)$ from both adjacent k-space scanning modules, wherein the direction of scanning of adjacent k-space scanning modules alternates.

DE 10 2011 086 369 A1 discloses a method for creating MR angiography images and a corresponding magnetic resonance device. The method relates to the creation of MR angiography images of a predetermined three-dimensional volume segment of a living object undergoing examination, using a magnetic resonance device. For this, the following acts are performed: magnetic resonance data in the volume segment is acquired by radial acquisition of a k-space; the magnetic resonance data is analyzed in order to subdivide the magnetic resonance data into groups, with each group including only the magnetic resonance data that corresponds to a particular heartbeat phase of the heart of the object undergoing examination; the MR angiography images are created on the basis of only the magnetic resonance data of one of these groups.

Robert Grimm, Sebastian Furst, Michael Souvatzoglou, Christoph Forman, Jana Hutter, Isabel Dregely, Sibylle I. Ziegler, Berthold Kiefer, Joachim Hornegger, Kai Tobias Block, Stephan G. Nekolla: Self-gated MRI motion modelling for respiratory motion compensation in integrated PET/MRI, in *Medical Image Analysis* 19, pp. 110-120 (2015), describes how accurate localization and uptake quantification of lesions in the chest and abdomen using PET imaging is challenged by respiratory difficulties during the examination. The paper describes how a so-called "stack-of-stars" MRI acquisition on integrated PET/MRI systems may be used to derive a high-resolution motion model, how many respiratory phases need to be differentiated, how much MRI scan time is required, and how the model may be employed for motion-corrected PET reconstruction. So-called MRI "self-gating" is applied to perform respiratory gating of the MRI data and simultaneously acquired PET raw data. After gated PET reconstruction, the MRI motion model is used to fuse the individual gates into a single, motion-compensated volume with high signal-to-noise ratio (SNR). The proposed method is evaluated in vivo for 15 clinical patients. The gating requires 5-7 bins to capture the motion to an average accuracy of 2 mm. With 5 bins, the motion-modeling scan may be shortened to 3-4 min. The motion-compensated reconstructions show significantly higher accuracy in lesion quantification in terms of standardized uptake value (SUV) and different measures of lesion contrast compared to ungated PET reconstruction. Furthermore, unlike gated PET reconstructions, the motion-compensated reconstruction does not lead to SNR loss.

Self-gating is described for example in: Robert Grimm, Simon Bauer, Berthold Kiefer, Joachim Hornegger, and Tobias Block: Optimal Channel Selection for Respiratory Self-Gating Signals, in 3ISMRM 21st Annual Meeting & Exhibition, SMRT 22nd Annual Meeting, 20-26 Apr. 2013, Salt Lake City, Utah, USA.

The GRASP technique is described for example in: Kai Tobias Block, Li Feng, Robert Grimm, Hersh Chandarana, Ricardo Otazo, Christian Geppert, Daniel K. Sodickson: GRASP: Tackling the Challenges of Abdominopelvic DCE-MRI, in *MAGNETOM Flash* May 2014, pp. 16-22; in: Philipp Riffel, Kai Tobias Block: Free-breathing DCE-MRI of the Kidney using GRASP, in *MAGNETOM Flash* (66) March 2016, pp. 56-58; or in: Li Feng, Kai Tobias Block, Robert Grimm, Hersh Chandarana, Sungheon Kim, Jian Xu, Leon Axel, Daniel K. Sodickson, Ricardo Otazo: Golden-Angle Radial Sparse Parallel MRI: Combination of Compressed Sensing, Parallel Imaging, and Golden-Angle Radial Sampling for Fast and Flexible Dynamic Volumetric MRI, in *Magn. Reson. Med.* 2014 September, vol. 72(3), pp. 707-17.

SUMMARY AND DESCRIPTION

The object of the disclosure is to provide a way of using magnetic resonance data that has been acquired by radial acquisition of a k-space to provide magnetic resonance images of higher temporal resolution and/or better image quality, in particular with smaller image artifacts, with the same predetermined duration of capture.

The scope of the present disclosure is defined solely by the appended claims and is not affected to any degree by the statements within this description. The present embodiments may obviate one or more of the drawbacks or limitations in the related art.

In order to achieve the object, a method is proposed for creating magnetic resonance (MR) tomography images of a predetermined three-dimensional volume segment of a living object undergoing examination, using a magnetic resonance device. The method includes the following acts: a) acquiring magnetic resonance data in the volume segment by radial acquisition of a k-space for a predetermined duration of capture that includes at least one full respiratory period of the object undergoing examination; b) analyzing the magnetic resonance data in order to determine therefrom at least one value of the at least one respiratory period; c) forming at least one data group that includes only the magnetic resonance data that belongs to at least one respiratory state of the at least one previously determined respiratory period of the object undergoing examination; and d) creating the magnetic resonance images from only the magnetic resonance data of the at least one data group.

This method has the advantage that, in act b), the respiratory period of the object undergoing examination is determined by experiment from the magnetic resonance data acquired or measured in act a), and is not previously predetermined in fixed manner or estimated. As a result, magnetic resonance data belonging to particular radial groups or "spokes" in the k-space may be more readily associated with a respective respiratory state. As a result, in turn, magnetic resonance images that correspond more accurately to the respiratory state and may thus give a higher temporal resolution and/or better image quality may be generated.

The living object undergoing examination may be a human, an animal, etc.

The magnetic resonance device may be a magnetic resonance capture device for acquiring or measuring the magnetic resonance data in accordance with act a) and a processing facility for performing acts b) to d). The magnetic resonance capture device and the processing facility may be integrated with one another to form a unit. As an alternative, the magnetic resonance device may be a distributed system. In this case, the magnetic resonance capture device and the processing facility may communicate with one another in particular by data link, in particular, practically in real time. The magnetic resonance capture device and the processing facility may be data-linked to one another by way of a network.

The predetermined duration of capture may be a duration of capture that includes at least one maximum respiratory period of the object undergoing examination, e.g., one or more respiratory periods each of 10 seconds for an adult human. With a duration of capture of 60 seconds, it is then possible to assume, with relatively good reliability, that it includes at least six respiratory cycles. The duration of capture may not correspond to exactly one or more actual respiratory cycles. The duration of capture may be predetermined automatically or by a person operating the magnetic resonance capture device or the magnetic resonance device, in particular, before the method is performed.

The quantity of magnetic resonance data that is acquired or measured over the duration of capture may also be designated a population of the magnetic resonance data.

In a development, the radial acquisition of the magnetic resonance data in a k-space that was performed in act a) is performed by the golden angle technique, in particular, the GRASP technique. In this technique, spokes may be acquired successively. The magnetic resonance data that belongs to a particular spoke may be acquired within a certain cohesive time period (e.g., within 200 milliseconds). The magnetic resonance data that belongs to a succeeding spoke may then be acquired, and so on. With a duration of capture of for example 60 seconds and a duration of 200 ms for each spoke, it is thus possible to acquire 300 spokes within the duration of capture. The spokes are acquired successively in relation to time, or serially, such that a temporal association with each spoke may be carried out within the duration of capture.

Act b) includes, in particular, analyzing the magnetic resonance data (e.g., all the acquired magnetic resonance data in the population, or some of it) in order to determine therefrom at least one actual (e.g., measured) respiratory period. The respiratory period may differ from the respiratory period assumed a priori in act a), for example, in respect of the duration(s) of respiration thereof. It is thus possible for a temporal location of the respiratory periods within the duration of capture to be determined more accurately.

The formation of a data group in act c) may include assignment of the radial acquisitions in the k-space (e.g., of specific spokes) that belong to the respiratory state. This may advantageously be performed respectively for each respiratory period in order to obtain a time characteristic of the magnetic resonance images, for example, in order to track the course of a contrast agent, (e.g., in the region of the abdomen), in order to perform an MR angiography, and so on.

In a development, for each respiratory period a respective data group is formed for the same respiratory state. As a result, for example, a time series of magnetic resonance images that belong to the same respiratory state may be created.

As an alternative or in addition, a plurality of temporally successive data groups may be formed for each respiratory period. As a result, it is possible to create for example a time series of magnetic resonance images that may represent a state of the object undergoing examination over the duration of capture, in particular also for different respiratory states.

Forming a data group may also be designated the grouping together or selection of a data group, or the filtering out of magnetic resonance data for this data group.

In a development, the at least one data group formed in act c) includes magnetic resonance data that belongs to a plurality of spokes in the k-space or includes a plurality of spokes in the k-space. It is thus possible, in particular, to group together all the magnetic resonance data belonging to a plurality of spokes into one data group. This is particularly advantageous because it allows image artifacts resulting from underscanning to be effectively reduced.

In act d), one or more magnetic resonance images may be generated from each data group. A particular magnetic resonance image is generated, in particular, from magnetic resonance data of a particular data group.

In one embodiment, in act b) a respective respiratory duration is determined for each respiratory period. This gives the advantage that magnetic resonance images having a particularly high imaging accuracy may be provided even if the respiratory periods of the living object undergoing examination are uneven or different.

In an embodiment that is advantageous for reducing processing complexity, in act b), an average value is determined for a plurality of respiratory durations. This is particularly advantageous if the respiratory periods used to form the average value are similar in duration. Within a duration of capture, specifically one average value may be determined from the individually determined respiratory durations. As an alternative, respective average values may be determined from different groups of individually determined respiratory durations.

In another embodiment, at least one respiratory state corresponds to a predetermined respiratory portion of the respiratory period. As a result, a particularly high temporal resolution and/or high image accuracy may be achieved, in particular, a high image accuracy with reduced streaking. The term "respiratory portion" may refer to a temporally cohesive part of a respiratory period. The respiratory portion may correspond to an inhalation state, an exhalation state, or a transitional state. The formation of at least one data group may then be achieved in that all the spokes that fall within the time of that respiratory portion of a respiratory period are added to the data group.

In a further embodiment, at least one respiratory portion corresponds to a fixedly predetermined relative position within the respiratory period. This further supports the achievement of a particularly high temporal resolution and/or high image accuracy. The respiratory portion may be defined by its duration (indicated, for example, as a percentage of the duration of the complete respiratory period, e.g., 45%), the time of its start in relation to the start or end of the respiratory period, and/or the time of its end in relation to the start or end of the respiratory period.

In another embodiment, the respiratory portion corresponds to a time portion of the respiratory period that is located around a maximum or a minimum of the respiratory amplitude, (e.g., a portion of predetermined absolute or relative length in relation to the duration of the respiratory period). This makes possible a particularly high temporal resolution and/or effective reduction of image artifacts (e.g., streaking and the like).

In yet another embodiment, the respiratory state corresponds to a respiratory amplitude. This advantageously also makes it possible to take into account whether the living object undergoing examination is breathing shallowly or not. This embodiment may be utilized to create magnetic resonance images independently of determining the actual respiratory period(s).

Moreover, in one embodiment, the number of radial acquisitions of the data group used to create a magnetic resonance image is increased if the respiratory amplitude lies below a predetermined amplitude threshold. This embodiment exploits the fact that with shallow breathing, (e.g., corresponding to a small respiratory amplitude), the organs in the body of the object undergoing examination move to a smaller extent than with deep breathing or large amplitude. Consequently, with shallow breathing more spokes may be used to build up a magnetic resonance image without appreciably reducing the image definition. Thus, advantageously the formation of image artifacts is reduced. Increasing the number of radial acquisitions of the data group corresponds, in particular, to increasing the number of spokes in the k-space used to generate a magnetic resonance image. This may be put into practice by adding all the spokes that fall into the time of a predetermined respiratory portion of a respiratory period to a data group, and in addition including the one or more succeeding spokes outside this respiratory portion.

In a variant, magnetic resonance images that are determined by a period duration that has been previously fixedly predetermined in conventional manner (which thus do not make use of determining the actual duration of the respiratory period) are prepared on the basis of an increased number of spokes if the respiratory amplitude is below a predetermined amplitude threshold.

Moreover, in one embodiment the minimum number of radial acquisitions (e.g., spokes) of the data group that is used to create a magnetic resonance image is 10, 11, 12, 13, or 15. This number of spokes is particularly advantageous in providing a high temporal resolution with image artifacts as a result of underscanning that are still acceptable.

The solution presented here further includes a computer program product that may be loaded directly into a memory of a digital computer, including program code parts suitable for performing acts of the method described here, in particular acts b) to d) thereof.

Furthermore, the above-mentioned problem is solved by a computer-readable storage medium, (e.g., any memory), including instructions that may be executed by a computer (e.g., in the form of program code) and that are suitable for the computer to perform acts of the method described here, in particular acts b) to d) thereof.

The object is also achieved by a processing facility, wherein the processing facility is intended to perform the method as described above. The processing facility may be a magnetic resonance device. The processing facility may also, however, be a unit separate from the magnetic resonance capture device, for example an evaluation station. In this case, the evaluation station may also be intended only to perform acts b) to d), while act a) is performed by the magnetic resonance capture device. As an alternative, the processing facility may be spatially integrated with the magnetic resonance capture device, in a magnetic resonance device.

The processing facility may in particular take the form of a processor unit and/or an at least partly hard-wired or logic circuit arrangement that is for example intended for the method as described herein to be performable, in particular acts b) to d) thereof. Said processing facility may be or include any kind of processor or computer having the accordingly required peripherals (e.g., memory, input/output interfaces, I/O devices, etc.). The processing facility may be a distributed processing facility, for example being distributed in the so-called "cloud".

The explanations above relating to the method apply accordingly to the apparatus. The apparatus may take the form of one component or be distributed over a plurality of components.

Likewise, the above-mentioned object is achieved by a system including at least one of the apparatuses described here.

BRIEF DESCRIPTION OF THE DRAWINGS

The above-mentioned properties, features and advantages of this disclosure, and the manner of achieving them, will be more clearly understood in conjunction with the schematic description below of an exemplary embodiment that is explained in more detail with reference to the drawings. Here, for the sake of clarity, like or equivalent elements may be provided with like reference numerals.

FIG. 2 depicts an exemplary sequence of a method for creating magnetic resonance images.

DETAILED DESCRIPTION

Figure 1:
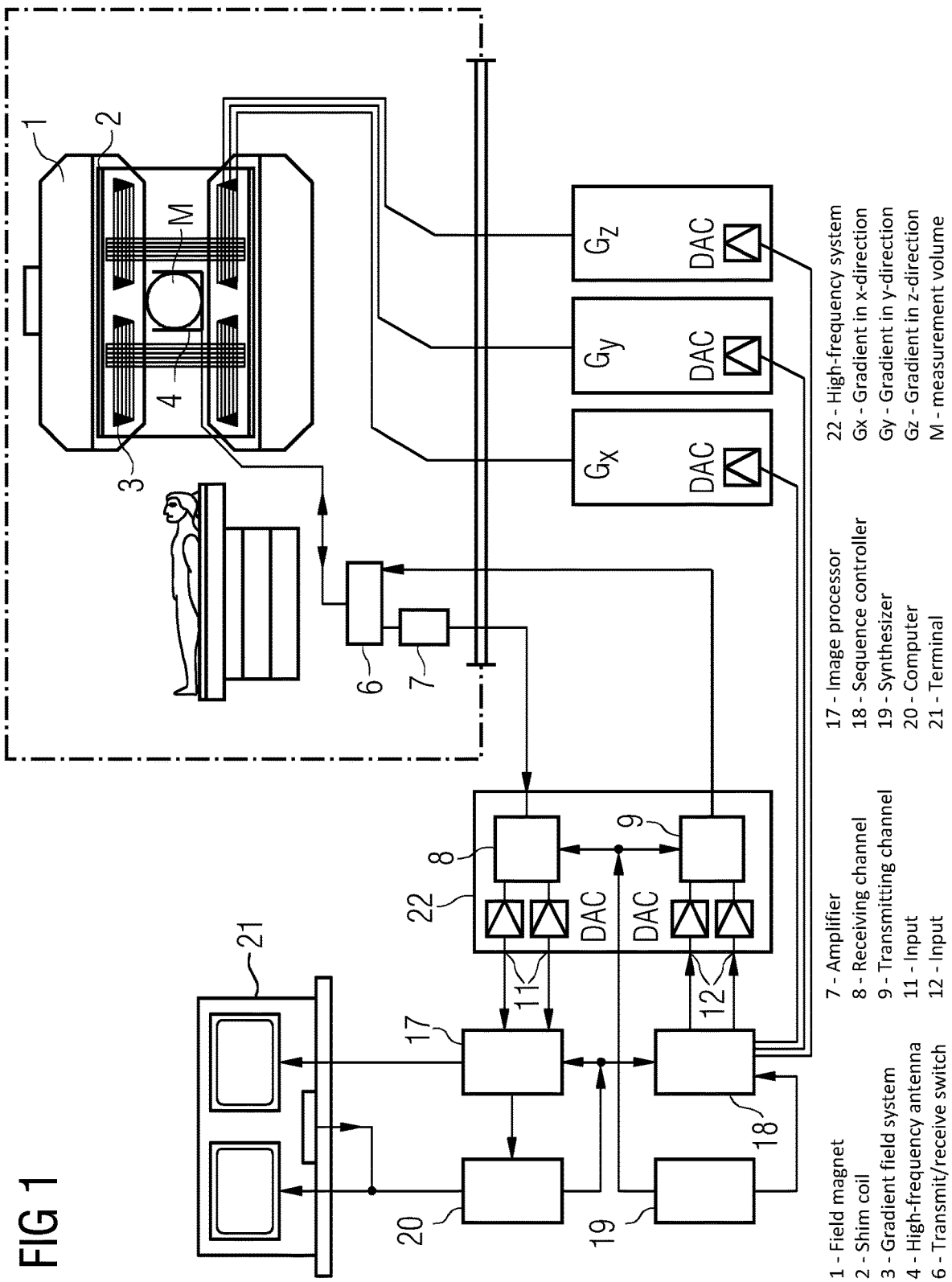
FIG. 1 depicts an exemplary nuclear spin tomography device.

FIG. 1 depicts an exemplary nuclear spin tomography device.

Figure 2:
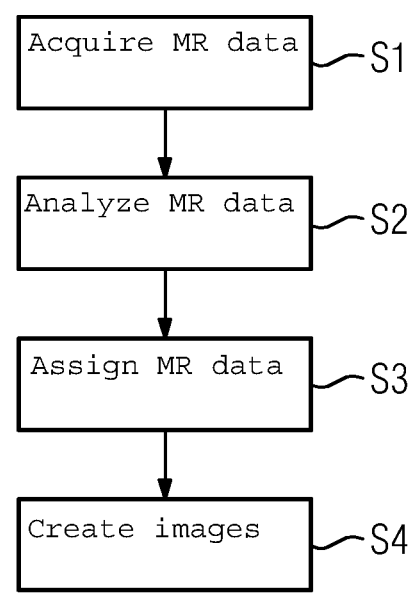
FIG. 2 depicts a sequence of an exemplary method for creating magnetic resonance images of a three-dimensional volume.

FIG. 2 depicts a sequence of an exemplary method for creating magnetic resonance images of a three-dimensional volume.

FIG. 2 depicts an exemplary sequence of a method for creating magnetic resonance images.

In act S1, magnetic resonance data is acquired radially in a k-space that corresponds to a three-dimensional volume segment from which the magnetic resonance images are to be created. In radial magnetic resonance data acquisition, the magnetic resonance data is acquired here spoke by spoke, in temporally successive acts. From this, the energy of the magnetic resonance data that was acquired for each spoke may be determined. Consequently, a Fourier transformation may be applied to the time characteristic of the previously determined energy for each spoke.

In act S2, the magnetic resonance data is analyzed in order to determine at least one respiratory period therefrom. This may be done, for example, on the basis of recognition of the fact that a volume of the lung is larger in a state after inhalation than in a state after exhalation, and so the associated frequency spectra and associated magnetic resonance images may consistently be allocated to a particular respiratory state. For example, magnetic resonance images in the state after inhalation are characterized by a particularly large dark area. In particular, in this way it is also possible for a time characteristic of a respiration event to be analyzed, as a result of which, in turn, the start, end and respiratory duration of a respiratory duration may be determined and measured. A plurality of respiratory durations of individual respiratory periods may be grouped together to give an average.

As an alternative or in addition, in act S2 the magnetic resonance data may be analyzed to determine therefrom a maximum respiratory amplitude of a respiratory period and/or to determine the spokes that belong to a respiratory amplitude below a predetermined threshold. In this way too, a point in time corresponding to a maximum or a minimum of the respiratory amplitude may be determined for each respiratory period.

In act S3, the magnetic resonance data is assigned to a plurality of data groups, for example, such that a particular data group includes only the magnetic resonance data that belongs to at least one respiratory state of a respective respiratory period. Thus, at least one respective data group is associated with each respiratory period. Act S3 may include an additional analysis of the magnetic resonance data, for example an allocation by frequency filtering.

A data group may include at least 10 spokes, 11 spokes, 12 spokes, 13 spokes, or 15 spokes.

In act S4, magnetic resonance images are created or reconstructed, such as images for illustrating the course of a contrast agent in the abdomen, wherein, in particular, only the magnetic resonance data that was selected for a data group is used for reconstruction of a magnetic resonance image. With continuous table motion, a stack of axial magnetic resonance images may be generated and then used to create an image of the arterial vessel system. In this case, an axial magnetic resonance image represents a slice of the volume segment that runs perpendicular to the direction of motion of the table.

FIG. 1 depicts a schematic illustration of a magnetic resonance device in the form of a magnetic resonance imaging or nuclear spin tomography device for generating a magnetic resonance image of a living object. Here, the construction of the nuclear spin tomography device corresponds to the construction of a conventional tomography device. A basic field magnet 1 generates a strong magnetic field that is constant over time, for polarizing or aligning nuclear spin in the region of an object that is to be examined, such as a part of a human body for examination. The high level of homogeneity of the basic magnetic field that is required for the nuclear magnetic resonance measurement is defined in a spherical measurement volume M into which the parts of the human body that are to be examined are introduced. As an aid to the requirement for homogeneity and, in particular, to eliminate factors that are invariable over time, so-called shim plates of ferromagnetic material are affixed at a suitable location. Factors that vary over time are eliminated by shim coils 2 that are controlled by a shim current supply 15.

A cylindrical gradient coil system 3, including three part-windings, is inserted into the basic field magnet 1. Each part-winding is supplied with current from an amplifier 14 in order to generate a linear gradient field in the respective direction of the Cartesian coordinate system. The first part-winding of the gradient field system 3 here generates a gradient Gx in the x-direction, the second part-winding generates a gradient Gy in the y-direction and the third part-winding generates a gradient Gz in the z-direction. Each amplifier 14 includes a digital-to-analog converter that is driven by a sequence controller 18 for the timely generation of gradient pulses.

Within the gradient field system 3, there is a high-frequency antenna 4 that converts the high-frequency pulses emitted by a high-frequency power converter to a magnetic alternating field for the purpose of exciting the nuclei and aligning the nuclear spin of the object to be examined or the region of the object to be examined. The high-frequency antenna 4 includes one or more HF transmitting coils and a plurality of HF receiving coils in the form of a linear arrangement of component coils. The HF receiving coils of the high-frequency antenna 4 also convert the alternating field from the precessing nuclear spin, (e.g., the nuclear spin echo signals brought about by a pulse sequence including one or more high-frequency pulses and one or more gradient pulses), into a voltage supplied by way of an amplifier 7 to a high-frequency receiving channel 8 of a high-frequency system 22. The high-frequency system 22 further includes a transmitting channel 9 in which the high-frequency pulses are generated for the purpose of exciting the nuclear magnetic resonance. Here, the respective high-frequency pulses are represented digitally in the sequence controller 18, as a sequence of complex numbers, on the basis of a pulse sequence predetermined by the device computer 20. This numerical sequence is supplied, as a real part and an imaginary part, by way of a respective input 12 to a digital-to-analog converter in the high-frequency system 22 and from this to a transmitting channel 9. In the transmitting channel 9, the pulse sequences are modulated to a high-frequency carrier signal whereof the base frequency corresponds to the resonant frequency of the nuclear spin in the measurement volume.

Switching over from transmitting to receiving mode is done by way of a transmit/receive switch 6. The HF transmitting coil of the high-frequency antenna 4 irradiates the measurement volume M with the high-frequency pulses for the purpose of exciting nuclear spin, and scans the resulting echo signals by way of the HF receiving coils. The nuclear resonance signals that are accordingly obtained undergo phase-sensitive demodulation in the receiving channel 8 of the high-frequency system 22 and are converted, using a respective analog-to-digital converter, into the real part and the imaginary part of the measurement signal. An image processor 17 reconstructs an image from the thus obtained measurement data. The measurement data, the image data and the control programs are managed by the device computer 20. The sequence controller 18 is pre-set with control programs in order to manage generation of the respectively desired pulse sequences and corresponding scanning of the k-space. In particular, the sequence controller 18 controls timely switching of the gradients, transmission of the high-frequency pulses of defined phase and amplitude, and receiving of the nuclear resonance signals. The time basis for the high-frequency system 22 and the sequence controller 18 is provided by a synthesizer 19. Appropriate control programs for generating a nuclear spin image are selected, and the generated nuclear spin image is displayed, via a terminal 21 that includes a keyboard and one or more screens.

A measurement method performed by the nuclear spin tomography device may be performed for example as in DE 103 37 932 A1.

The image processor 17, the device computer 20 and/or the terminal 21 may be components of a processing facility for performing at least acts S2 to S4 from FIG. 2.

The terminal 21 may be equipped with a computer-readable storage medium (such as a USB stick, a removable disk, a cloud memory, etc.) for the purpose of communication.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for creating magnetic resonance images of a predetermined three-dimensional volume segment of a living object undergoing examination, using a magnetic resonance device, the method comprising:
   acquiring magnetic resonance data in the three-dimensional volume segment by radial acquisition of a k-space for a predetermined duration of capture that includes at least one full respiratory period of the living object undergoing examination;
   analyzing the magnetic resonance data in order to determine at least one respiratory period;
   forming at least one data group that includes only the magnetic resonance data that belongs to a respiratory portion of the at least one respiratory period; and
   creating the magnetic resonance images from only the magnetic resonance data of the at least one data group.

2. The method of claim 1, wherein, in the analyzing of the magnetic resonance data, a respective respiratory duration is determined for each respiratory period of the at least one respiratory period.

3. The method of claim 2, wherein, in the analyzing of the magnetic resonance data, an average value is determined for a plurality of respective respiratory durations.

4. The method of claim 1, wherein, in the analyzing of the magnetic resonance data, an average value is determined for a plurality of respective respiratory durations.

5. The method of claim 1, wherein the respiratory portion corresponds to a fixedly predetermined relative position within the respiratory period.

6. The method of claim 1, wherein the respiratory portion corresponds to a portion of predetermined relative length that is located around a maximum or a minimum of a respiratory amplitude.

7. The method of claim 1, wherein the respiratory portion corresponds to a respiratory amplitude.

8. The method of claim 6, wherein a number of radial acquisitions of the data group used to create a magnetic resonance image is increased when the respiratory amplitude lies below a predetermined amplitude threshold.

9. The method of claim 7, wherein a number of radial acquisitions of the data group used to create a magnetic resonance image is increased when the respiratory amplitude lies below a predetermined amplitude threshold.

10. The method of claim 1, wherein a minimum number of radial acquisitions of the data group used to create a magnetic resonance image is 10.

11. The method of claim 1, wherein a minimum number of radial acquisitions of the data group used to create a magnetic resonance image is 15.

12. A non-transitory computer readable medium storing thereon a computer program configured to be loaded directly into a memory of a digital computer of an apparatus, wherein the computer program, when executed by the digital computer, is configured to cause the apparatus to:
   acquire magnetic resonance data in a volume segment by radial acquisition of a k-space for a predetermined duration of capture that includes at least one full respiratory period of an object undergoing examination;
   analyzing the magnetic resonance data in order to determine at least one respiratory period;
   forming at least one data group that includes only the magnetic resonance data that belongs to a respiratory portion of the at least one respiratory period; and
   creating magnetic resonance images from only the magnetic resonance data of the at least one data group.

13. A processing facility comprising:
   at least one processor; and
   at least one memory including computer program code for one or more programs, the at least one memory and the computer program code configured to, with the at least one processor, cause the processing facility to at least perform:
   acquire magnetic resonance data in a volume segment by radial acquisition of a k-space for a predetermined duration of capture that includes at least one full respiratory period of an object undergoing examination;
   analyzing the magnetic resonance data in order to determine at least one respiratory period;
   forming at least one data group that includes only the magnetic resonance data that belongs to a respiratory portion of the at least one respiratory period; and
   creating magnetic resonance images from only the magnetic resonance data of the at least one data group.

14. The method of claim 1, wherein the respiratory portion is an inhalation state, an exhalation state, or a transitional state of the respiratory period.

* * * * *